United States Patent
Mayo et al.

(10) Patent No.: US 10,877,027 B2
(45) Date of Patent: Dec. 29, 2020

(54) DEVICE AND METHOD FOR DETECTING A TARGET ANALYTE

(71) Applicants: John Mayo, Nashville, TN (US); Kevin Jones, Knoxville, TN (US)

(72) Inventors: John Mayo, Nashville, TN (US); Kevin Jones, Knoxville, TN (US)

(73) Assignee: Webb Diagnostics Technologies, Inc., Nashville, TN (US)

( * ) Notice: Subject to any disclaimer, the term of this patent is extended or adjusted under 35 U.S.C. 154(b) by 142 days.

(21) Appl. No.: 15/665,955

(22) Filed: Aug. 1, 2017

(65) Prior Publication Data

US 2018/0030125 A1    Feb. 1, 2018

Related U.S. Application Data

(60) Provisional application No. 62/369,868, filed on Aug. 2, 2016, provisional application No. 62/369,554, filed on Aug. 1, 2016.

(51) Int. Cl.
*G01K 17/00*     (2006.01)
*G01N 33/53*     (2006.01)
(Continued)

(52) U.S. Cl.
CPC ......... *G01N 33/5304* (2013.01); *C07K 14/47* (2013.01); *C07K 16/08* (2013.01);
(Continued)

(58) Field of Classification Search
CPC ........... G01N 33/5304; G01N 33/6893; G01N 33/02; G01N 33/18; G01N 2001/022;
(Continued)

(56) References Cited

U.S. PATENT DOCUMENTS

| 2009/0123336 A1 | 5/2009 | Yang et al. |
| 2015/0079583 A1* | 3/2015 | Baudenbacher .. B01L 3/502784 435/5 |
| 2016/0186166 A1* | 6/2016 | Poehmerer ........ B01L 3/502761 205/420 |

FOREIGN PATENT DOCUMENTS

| EP | 155529 A2 | 7/2005 |
| WO | 2015027151 A1 | 2/2015 |
| WO | WO2016094512 A1 | 6/2016 |

OTHER PUBLICATIONS

Herrmann et al. Enzymatically-generated fluorescent detection in micro-channels with internal magnetic mixing for the development of parallel microfluidic ELISA. Lab on a Chip. vol. 6 (4): 555-560 (Mar. 2006).*

(Continued)

*Primary Examiner* — Gailene Gabel
(74) *Attorney, Agent, or Firm* — Craig A. Phillips; Dickinson Wright PLLC

(57) ABSTRACT

A device and method for detecting the presence of a target analyte in a fluid sample are provided. The device can include an inclined capillary tube for transporting a sample fluid containing a sample and functionalized magnetic beads. The functionalized magnetic beads capture the target analyte from the sample fluid. A well is coupled with the inclined capillary tube for containing a developer solution and for receiving the sample fluid. In at least one embodiment a magnet is movably attached to the inclined capillary tube for attracting the magnetic beads of the sample fluid and moving the magnetic beads into the well. A calorimeter is disposed adjacent to the well for receiving heat output from a reaction caused by an enzyme reaction associated with the captured target analyte in the developer solution thereby allowing detection and quantification of the target analyte.

7 Claims, 5 Drawing Sheets

(51) Int. Cl.

| | |
|---|---|
| *C07K 14/47* | (2006.01) |
| *C07K 16/08* | (2006.01) |
| *C07K 16/18* | (2006.01) |
| *C07K 16/44* | (2006.01) |
| *G01N 33/02* | (2006.01) |
| *G01N 33/18* | (2006.01) |
| *G01N 33/68* | (2006.01) |
| *B01L 3/00* | (2006.01) |
| *A61K 39/00* | (2006.01) |
| *G01N 1/02* | (2006.01) |
| *G01N 33/00* | (2006.01) |

(52) U.S. Cl.
CPC .............. *C07K 16/18* (2013.01); *C07K 16/44* (2013.01); *G01N 33/02* (2013.01); *G01N 33/18* (2013.01); *G01N 33/6893* (2013.01); *A61K 2039/505* (2013.01); *B01L 3/5027* (2013.01); *C12Q 2600/158* (2013.01); *G01N 2001/022* (2013.01); *G01N 2001/028* (2013.01); *G01N 2033/0096* (2013.01)

(58) Field of Classification Search
CPC ..... G01N 2001/028; G01N 2033/0096; C07K 16/18; C07K 14/47; C07K 16/08; C07K 16/44; A61K 2039/505; B01L 3/5027; C12Q 2600/158; G01K 17/00
See application file for complete search history.

(56) References Cited

OTHER PUBLICATIONS

Funano, S. et al., "Capillary-based enzyme-linked immunosorbent assay for highly sensitive detection of thrombin-cleaved osteopontin in plasma", Anal. Biochem., vol. 440, Jun. 2, 2013; pp. 137-141.

Herrmann, M. et al., "Enzymatically-generated fluorescent detection in micro-channels with internal magnetic mixing or the development of parallel microfluidic ELISA", Lab on a Chip, vol. 6, Mar. 3, 2006; pp. 555-560.

Jamshaid, T. et al., "Magnetic particles: From preparation to lab-on-a-chip, biosensors, microsystems and microfluidics applications", Trends in Analytical Chemistry, vol. 79, May 1, 2016; pp. 344-362.

Larraneta, E. et al., "A proposed model membrane and test method for microneedle insertion studies", International Journal of Pharmaceutics, vol. 472, May 28, 2014, pp. 65-73.

Lin, S., "A Study of Bifurcation Design used in CD-ELISA Micro-Fluidic Platform", Proceedings of ASME 2010 First Global Congress on NanoEngineering for Medicine and Biology, Feb. 10, 2010; p. 1, 1st column, 1st paragraph, (two pages).

Proczek, G. et al., "Total serum IgE quantification by microfluidic ELISA using magnetic beads", Anal. Bioanal. Chem., vol. 402, Oct. 22, 2011; pp. 2645-2653.

International Search Report and Written Opinion dated Oct. 13, 2017 in corresponding PCT International Patent Application No. PCT/US2017/044941 (twelve pages).

Search Report regarding related EP App. No. 17837556.4; dated Oct. 28, 2020.

* cited by examiner

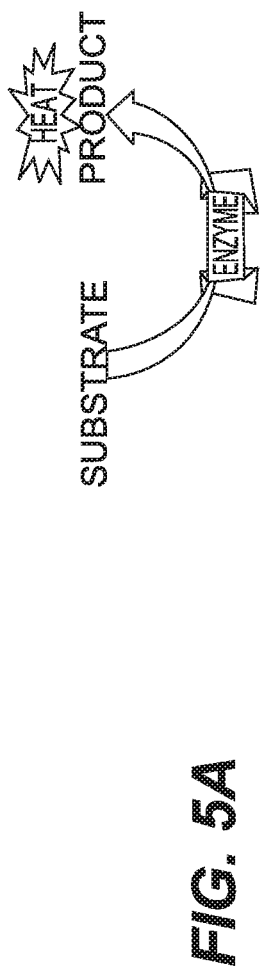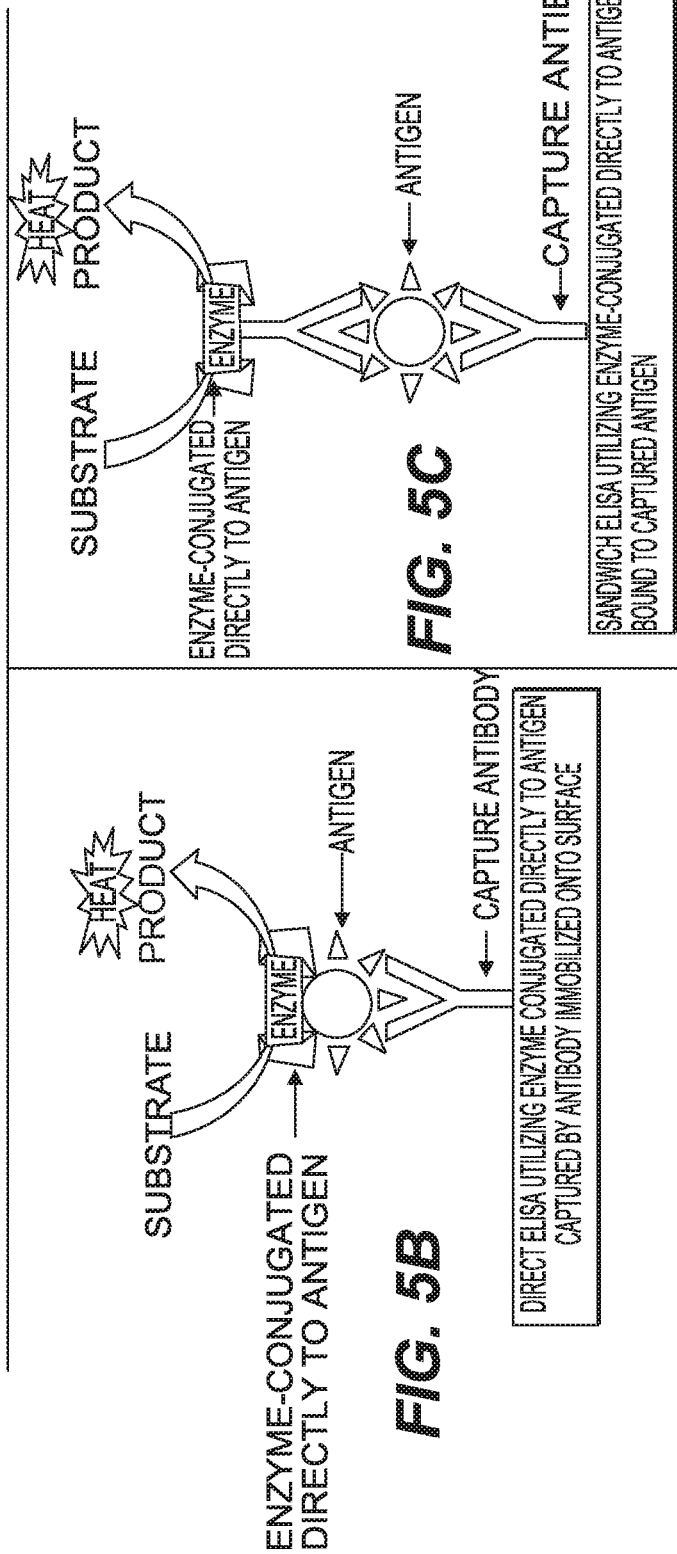
FIG. 5A
FIG. 5B
FIG. 5C

DEVICE AND METHOD FOR DETECTING A TARGET ANALYTE

RELATED APPLICATIONS

This application claims the benefit of U.S. Provisional Application No. 62/369,554 filed Aug. 1, 2016 and of U.S. Provisional Application No. 62/369,868 filed Aug. 2, 2016.

STATEMENT REGARDING FEDERALLY SPONSORED RESEARCH

None.

FIELD

The present disclosure relates generally to diagnostic devices and methods for rapid, inexpensive, highly sensitive and specific detection of target analytes using nanocalorimetry with a functionalized surface to capture analytes for use in a variety of settings and industries, such as healthcare, agriculture, food industry, veterinary, drug discovery, defense and homeland security. The present disclosure further relates to a thermal enzyme-linked immunosorbent assay (ELISA) system utilizing a nanocalorimeter and magnetic beads.

BACKGROUND

This section provides background information related to the present disclosure which is not necessarily prior art.

Currently there is no completely integrated, affordable, point-of-care (POC) or point-of-need diagnostic platform that is rugged, durable, and that provides results in minutes with a high level of sensitivity and specificity that may be operated with little training. This problem applies to diagnosing/detecting bacteria, viruses, fungi, pathogens, biomarkers and various chemicals, as well as chemical and biological warfare agents. Existing diagnostic platforms are very expensive in terms of both the equipment and the actual test performed, require a laboratory or hospital setting, require highly trained technicians, require expensive infrastructure, and take from hours to days to obtain results. This current time to deliver results and the current cost of getting these results ultimately means lost lives, health, and money when utilizing current technologies.

Recent development with existing detection technologies of biological binding events and cellular activity have improved over time to the point where they are now limited by the first principles of the binding affinity of the targets or targeted pairs (e.g., antibody-antigen, etc.), or the amount of cellular activity when measuring metabolic activity. The weaker binding events and lower cellular metabolic rates are below the noise floor of these technologies, however, thereby rendering it hard to impossible to detect such events as those limits are reached.

Enzyme-linked immunosorbent assay (ELISA) systems are known in the art and are used to detect the presence of an analyte in a sample through antigen-antibody binding followed by an enzyme reaction and thereby detection of the binding event. In a conventional ELISA system enzyme-conjugated reagents, substrates and color developers are used to produce a visible or fluorescent signal that is detected optically, typically using very expensive optical systems. The typical sample volume is limited to 5 to 100 microliters and the process can be expensive.

Accordingly, there remains a need for improved diagnostic devices and methods for rapid, inexpensive, highly sensitive and specific detection of target analytes without shortcomings as described above.

It is desirable to provide a method and system that will allow for processing of much larger sample volumes, a simpler detection process at a lower cost and an ability to carry out multiplexing assays for detection of more than one analyte in a sample.

SUMMARY OF THE DISCLOSURE

This section provides a general summary of the disclosure and is not a comprehensive disclosure of its full scope or all features, aspects or objectives.

In general terms, this disclosure provides an enhanced ELISA method for detection of target analytes using a calorimeter and magnetic beads.

In at least one embodiment the present disclosure is a system for detection of a target analyte by an Enzyme-Linked Immunosorbent Assay (ELISA) comprising: a capillary tube that includes a first end and a second end and a well located between the first end and the second end; a calorimeter attached to the well, the calorimeter adapted to detect a change in a temperature in the well; and a magnet.

In at least one embodiment the magnet is movable along an outside of the capillary tube and the well and wherein the magnet can move magnetic beads from the first end to inside the well.

In at least one embodiment the magnet is secured to a bottom of the well, the magnet capable of attracting magnetic beads from the capillary tube into the well.

In at least one embodiment the well further includes a frangible protective film over an opening of the well and wherein the opening connects the well to the capillary tube.

In at least one embodiment the system further comprises a button and a puncture needle, the button and puncture needle capable of breaking the frangible film to allow communication between an inside of the capillary tube and the well.

In at least one embodiment the system includes a plurality of magnetic beads, the beads capable of binding a target analyte.

In at least one embodiment the magnet is an electormagnet.

In at least one embodiment the system is reusable.

In at least one embodiment the present disclosure is a system for detection of a target analyte by an Enzyme-Linked Immunosorbent Assay (ELISA) comprising: a capillary tube that includes a first end and a second end and a well located between the first end and the second end; a calorimeter attached to the well, the calorimeter adapted to detect a change in a temperature in the well; and a plurality of capture antibodies located in the well the capture antibodies binding to one of a target analyte or an antibody to the target analyte.

In at least one embodiment the present disclosure is a system for detection of a target analyte by an Enzyme-Linked Immunosorbent Assay (ELISA) comprising: a main body having a flow splitter, the flow splitter connected to a plurality of channels; each of the channels including a capillary tube having a first end and a second end with a porous matrix adjacent to the first end and a well located between the porous matrix and the second end, the porous matrix containing a label with the label capable of binding to a specific target analyte, the label optionally is conjugated to a magnetic bead; a calorimeter attached to the well, the calorimeter adapted to detect a change in a temperature in the well; and at least one of a plurality of capture antibodies located in the well or a magnet associated with the well, wherein the capture antibodies bind to one of the label or the analyte and wherein the magnet can capture the label conjugated to a magnetic bead.

In at least one embodiment at least one of the porous matrixes in one of the capillary tubes contains a label that binds to a different analyte than another label in another of the porous matrixes.

In at least one embodiment all of the porous matrixes in all of the capillary tubes contain a label that binds to the same analyte.

In at least one embodiment each of the labels in the porous matrixes is bound to an enzyme.

In at least one embodiment the disclosure is a method of detection of a target analyte by an Enzyme-Linked Immunosorbent Assay (ELISA) comprising the steps of: a. mixing a plurality of functionalized magnetic beads with a sample containing the analyte to form a solution and binding the analyte to the magnetic beads in the solution; b. providing a capillary tube that includes a first end and a second end and a well located between the first end and the second end; a calorimeter attached to the well, the calorimeter adapted to detect a change in a temperature in the well; and a magnet; c. putting the solution into the capillary tube and using the magnet to capture the magnetic beads and to position the magnetic beads in the well; d. exposing the magnetic beads with attached analyte to an antibody to the analyte, the antibody linked to an enzyme, thereby binding the antibody to the analyte; and e. adding to the well a substrate for the enzyme and measuring the change in temperature in the well as a result of the enzyme acting on the substrate.

In at least one embodiment the disclosure is a method of detection of a target analyte by an Enzyme-Linked Immunosorbent Assay (ELISA) comprising the steps of: a. providing a system comprising: a main body having a flow splitter, the flow splitter connected to a plurality of channels; each of the channels including a capillary tube having a first end and a second end with a porous matrix adjacent to the first end and a well located between the porous matrix and the second end, the porous matrix containing a label with the label capable of binding to the target analyte, the label optionally conjugated to a magnetic bead; a calorimeter attached to the well, the calorimeter adapted to detect a change in a temperature in the well; and at least one of a plurality of capture antibodies located in the well or a magnet associated with the well, the capture antibodies capable of binding to one of the label or the analyte and the magnet capable of capturing the label conjugated to a magnetic bead; b. adding a sample containing the target analyte to the flow splitter and flowing the sample through a plurality of the channels, the target analyte binding to the label in at least one of the capillary tubes in in at least one of the channels; c. capturing the target analyte with the bound label in the well associated with the capillary tube with at least one of the capture antibodies or the magnet; d. detecting the presence of the target analyte in the well by measuring a change in the temperature in the well resulting from an enzyme reaction in the well, the enzyme associated with the target.

In at least one embodiment the method further comprises the step of providing a sample containing a plurality of different analytes and further providing a system wherein each of the capillary tubes contains a different label directed to one of the analytes and each well containing capture antibodies to capture the target analyte with label attached to it is associated with the capillary tube.

BRIEF DESCRIPTION OF THE DRAWINGS

The drawings described herein are for illustrative purposes only of selected embodiments and not all possible implementations, and are not intended to limit the scope of the present disclosure.

FIG. 4B shows a more detailed view of one of the channels of the flow splitter shown in FIG. 4A; and FIG. 5A shows a schematic diagram of heat produced by action of an enzyme on its substrate, FIG. 5B shows a schematic diagram of a direct ELISA system and production of heat according to the present disclosure and FIG. 5C shows a schematic diagram of a capture ELISA system and production of heat that can occur using an enzyme and capture antibodies according to aspects of the present disclosure.

DETAILED DESCRIPTION

Figure 1:
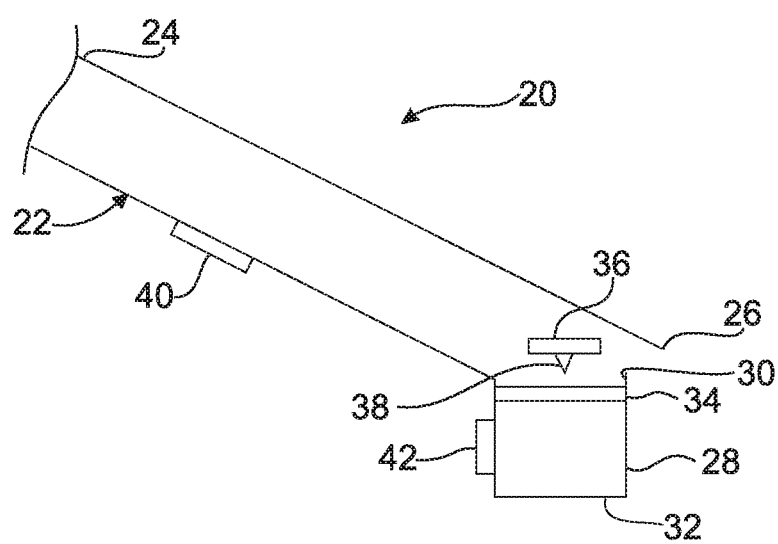
FIG. 1 illustrates a first embodiment of a device for detecting a target analyte according to aspects of the present disclosure.

In the following description, details are set forth to provide an understanding of the present disclosure. In some instances, certain circuits, structures and techniques have not been described or shown in detail in order not to obscure the disclosure.

In general, the present disclosure relates to a device and method for detecting a target analyte of the type well-suited for use in many applications. The device and method for detecting a target analyte of this disclosure will be described in conjunction with one or more example embodiments. However, the specific example embodiments disclosed are merely provided to describe the inventive concepts, features, advantages and objectives will sufficient clarity to permit those skilled in this art to understand and practice the disclosure Referring to the Figures, wherein like numerals indicate corresponding parts throughout the several views, devices and methods for detecting a target analyte are disclosed.

In general terms, in at least one embodiment this invention provides a thermal ELISA system that also utilizes magnetic beads as the capture surface for the target analyte or antigen. In the present specification and claims the terms target, target analyte and antigen mean the same thing namely the entity being detected and measured. In a typical ELISA Direct assay the target antigen is exposed to the capture surface, for example polystyrene, and the antigen/target is adsorbed by passive adsorption. It is known to create ELISA surfaces that are hydrophilic or hydrophobic depending on the nature of the target antigen. The three basic type of ELISA are: Direct assay, Indirect assay and Capture assay. All three can benefit from the present disclosure as described herein. Each will be described briefly here.

In the Direct assay the antigen/target is first exposed to a surface that is binds to by passive adsorption, for example, a polystyrene or modified polystyrene surface. The bound antigen is washed to remove unbound antigen. Then an antibody to the antigen is added, this antibody is an enzyme-linked antibody. Finally, reagent for the enzyme is added and the developed color is measured to determine the presence and quantity of the antigen/target. In an Indirect assay the antigen/target is again first bound to a functionalized surface, usually by passive adsorption, like a polystyrene or other binding surface. Then after a washing process to remove unbound antigen the surface is exposed to a primary antibody against the target/analyte. Then after further washing the system is exposed to a secondary antibody that is specifically direct against the primary antibody and that is an enzyme-linked antibody. Finally, as above the reagent for the enzyme is added and the reaction followed by color development. In a Capture assay the surface is first functionalized with an antibody that is specific for the target/analyte and upon exposure to a sample containing the analyte it "captures" the target/antigen. Then after washing away unbound material the surface with bound antigen is exposed to a primary antibody against the antigen. The primary antibody can either be an enzyme-linked antibody or not, if it is not then another step is necessary. In the additional step a secondary enzyme-linked antibody against the primary antibody is exposed to the surface. Finally, reagent for the enzyme is added and the reaction followed by color development. All of the prior processes rely on color development to detect the presence of the target analyte. The thermal process of the present disclosure is less expensive than the common optical process and is simpler. In the thermal process a voltage readout is generated that is indicative of the heat generated from the reaction of the linked enzyme with its reagent which is detected by the nanocalorimeter. The volumes used in the thermal detection are very small which enhances surface charges and reduces the matrix sample effects compared to conventional ELISA assays. The process uses magnetic beads with a functionalized surface to capture the antigen/analyte and for movement of the captured antigen/analyte through the process. The functionalization can include polystyrene coatings and other known functionalization surfaces. Magnetic beads can be easily functionalized with a variety of surface treatments. The magnetic beads are functionalized with a bound entity that can bind to the target analyte. Such functionalized magnetic beads are known in the art and will not be described in detail. The functionalization can include binding to the beads an entity that includes an antibody to the target analyte or that recognizes a target analyte after the target analyte has been bound to an antibody to the target analyte. This eliminates the need for a microfluidics delivery system to deliver the components to the reaction volume. So the procedure in the present disclosure can process much higher volumes of sample than both traditional ELISA and microfluidics ELISA processes. The bead-based capture system allows for very large volumes of sample to be screened and then analyzed by thermal ELISA.

The bead based Thermal ELISA system of the present invention combines micromachined calorimeters for the thermal detection with a bead-based sample delivery system. The technology can replace the more expensive conventional ELISA systems with an inexpensive, rapid, rugged point of care device that will require minimal human intervention, sample handling and sample processing. The present system can be used in Direct ELISA assay systems, Indirect ELISA assay systems and Capture or Sandwich ELISA systems. As is known in the art each of these systems has several variations that will not be further discussed herein as they are well known. The thermal ELISA system according to the present invention combines calorimeters, with a fluid processing system and magnetic beads as carriers. The magnetic beads are functionalized to capture and extract analytes from a sample solution. Using magnetic forces the magnetic beads with the bound analytes are collected and then processed in different solutions and washes and then subjected to a detection assay to generate a heat signature when delivered to a reaction volume of a calorimeter.

A first embodiment of a device 20 for detecting a target analyte shown in FIG. 1 includes a capillary tube 22 extending from a first end 24 to a second end 26. In one embodiment as shown, the first end 24 is elevated above the second end 26 to create an inclined capillary tube 22 for transporting a sample fluid containing a targeted analyte and magnetic beads that have been functionalized to identify and bind to the target analyte. The sample can be any biological sample such as, but not limited to whole blood, serum, plasma, CSF, saliva, and milk. It should also be appreciated that the sample could also be any fluid that contains a targeted analyte (e.g., water, buffer). While the inclined capillary tube 22 is identified and illustrated as being inclined, it should be understood that this is simply an example of a capillary or channel with a force to drive liquid through the channel. In the example of an inclined capillary tube 22 or channel, the motive force to drive the liquids through is the effect of gravity on a channel that is elevated on one end versus the other end. However in other designs the inclined capillary tube 22 could be level (i.e., not inclined) or even going upwards with the force to drive the liquids being a different force, for example, but not limited to, air pressure or electromotive force. The sample being tested for the presence of the analyte is mixed with a portion of the functionalized magnetic beads and allowed to incubate for a period of time so the functionalized beads can capture the target analyte, and then the sample with the beads is introduced into the first end 24 of the capillary tube 22.

A well 28 having an open end 30 and a closed end 32 is coupled with the second end 26 of the inclined capillary tube 22 at the open end 30. The well 28 contains a developer solution and is for receiving the magnetic beads with attached analyte. A protective film 34, that is frangible, is disposed over the open end 30 of the well 28 for sealing the well 28. A button 36 that has a puncturing tip such as a needle 38 attached thereto is arranged adjacent the protective film 34 for selectively breaking the protective film 34 and allowing the fluid sample and magnetic beads to enter the well 28. For example, downward movement of the button 36 can cause the needle 38 to puncture the protective film 34 and allow the sample fluid and magnetic beads to enter the well 28.

A magnet 40 is movably attached to the inclined capillary tube 22 between the first and the second ends, 24 and 26, for attracting the magnetic beads from the sample fluid. The magnet 40 also provides movement of the magnetic beads into the well 28 in response to movement of the magnet 40 toward the well 28 (i.e., movement of the magnet 40 along the inclined capillary tube 22 also moves the magnetic beads 40 within the sample fluid. In all embodiments described in the present specification it is understood that the magnet 40 may comprise an electromagnet. It should be understood that while a magnet 40 with a constant magnetic field may be employed, a programmable magnet that is capable of producing a variable magnetic field (i.e., a magnet that can have its magnetic field manipulated or programmed) can be used alternatively. A variable magnetic field can be made more evenly distributed over a wider area in order to avoid any clumping effect that may reduce the surface area of the magnetic beads (e.g., if a normal rare Earth magnet 40 having a native magnetic field structure is used). For example, programmable magnets 40 such as those discussed at https://en.wikipedia.org/wiki/Programmable magnet 40 could be used. It is envisioned that a programed magnetic field would result in the ability to generate a thinner layer of magnetic beads than is seen traditionally. The use of a traditional magnet often results in a tightly bound "clump" or "cluster" of particles, the tight packing only allows reagents to access the outside of the clump or cluster. The use of a programmed magnet limits the magnets field such that clusters or clumps do not occur and results in the formation of "layers" of particles with a defined "depth" of the layer. The production of layers with defined depth can result a far greater accessible surface area then can be seen with the clumps or clusters that are seen with traditional magnets.

A calorimeter 42 is disposed adjacent to the well 28 for receiving heat output from a reaction between the enzyme-linked on the antibody that identifies the target analyte and the developer solution. The calorimeter 42 may, for example, convert the heat output to electricity which can then be read by a measuring device (not shown). The system as described has a special advantage in that it can be washed and reused. The magnet 40 can be used to move the tagged analyte through the entire system and out of the system. Then the system can be washed and completely reused. This provides a very cost effective system unlike prior art systems which are single use systems.

A method of operating the first embodiment 20 of the device is also provided. The method includes the steps of: mixing the sample and a plurality of functionalized magnetic beads together to form a sample fluid and allowing a period of time for the functionalized magnetic beads to bind any target analyte that is present in the sample. Alternatively, the functionalized beads can be pre-loaded into the capillary tube 22 and the sample is poured into the tube 22 where it passes over the functionalized magnetic beads, which capture any target analyte. The method proceeds by introducing the sample fluid with magnetic beads having bound to them target analyte into the inclined capillary tube 22. Then, the next step is capturing the magnetic beads with a magnet 40 adjacent the inclined capillary tube 22. The method continues with the steps of adding at least one wash to the inclined capillary tube 22 and adding a label to bind to the analyte on the magnetic beads trapped on the magnet 40. The label can be either an enzyme-linked antibody or other binding species, a large protein or similar material that is labelled with antibody and linked to an enzyme, or a bead (e.g., Polystyrene PS) that is labelled with an antibody and linked to an enzyme. The label binds to the analyte to identify its presence on the magnetic beads. The advantage of the latter two formats is that significant amplification may be realized via the use of a labelled protein or beads. The wash is typically a buffer that may or may not contain surfactants and polymers. The wash has a defined buffer capacity, pH and ionic strength to minimize any nonspecific binding of materials that may give rise to false signals. Then the method includes the step of pushing the button 36 to break the protective film 34 over the well 28 prefilled with a developer solution. The method continues by moving the magnet 40 along the inclined capillary tube 22 and transporting the magnetic beads with bound target analyte and second label which included a linked enzyme into the developer solution in the well 28. The method then includes the step of reacting the linked enzyme, which is bound to the analyte through one of the above methods, in the developer solution with its substrate. The method then includes the step of measuring heat generated by the reaction between the linked enzyme and the developer solution using a calorimeter 42. As known the reaction can actually be a reaction carried out by an enzyme bound to an antibody that is specific for the target analyte as in a typical ELISA reaction. This magnetic bead-analyte-antibody-enzyme conjugate will generate a thermal signal when exposed to the reaction solution that is indicative of the quantity of the target analyte. The difference being that rather than monitoring color development from the reaction one just measures the heat generated by the reaction. This is much more sensitive than measuring color development. The first method concludes by confirming presence of the target analyte in the sample fluid by measuring of the heat of reaction by the calorimeter 42. As discussed above, this system of a capillary tube 22, well 28, magnet 40, calorimeter 42 and magnetic beads to trap the analyte can be used in a Direct assay, an Indirect assay and a Capture assay according to general ELISA procedures. The system allows for adaptation to any of these three procedures.

Figure 2:
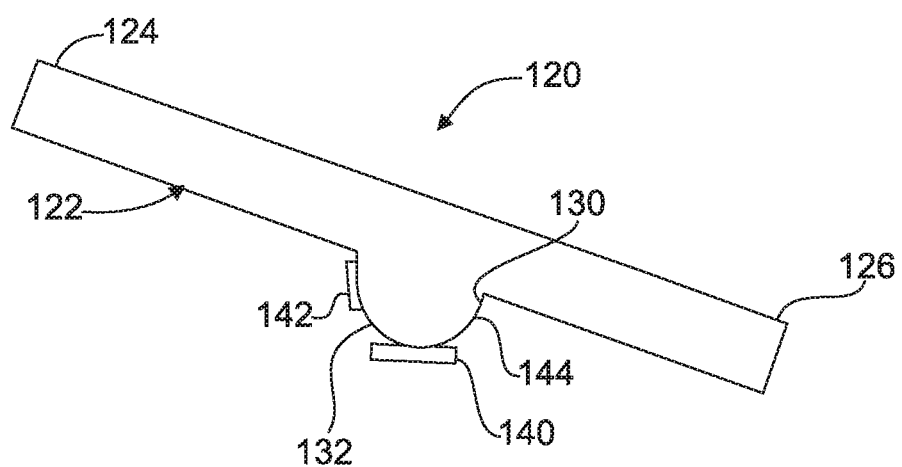
FIG. 2 illustrates a second embodiment of a device for detecting a target analyte according to aspects of the present disclosure.

A second embodiment 120 of a device for detecting a target analyte is shown in FIG. 2 and includes an inclined capillary tube 122 extending from a first end 124 to a second end 126. Specifically, the first end 124 is elevated above the second end 126 for transporting a sample fluid containing a sample and functionalized magnetic beads.

A defined volume well 144 has an open end 130 and a closed end 132 and is coupled with the inclined capillary tube 122. The defined volume well 144 is disposed between the first end 124 and the second end 126 for receiving the sample fluid with the functionalized magnetic beads. A magnet 140 is attached to the defined volume well 144 for attracting and holding the magnetic beads from the sample fluid.

A calorimeter 142 is disposed adjacent to the defined volume well 144 for receiving heat output from a reaction between the bead-analyte-antibody-enzyme conjugate and the developer solution as described above. This system is also completely reusable as discussed above and provides special advantages over the prior art.

A method of operating the second embodiment 120 of the device is also provided. The method includes the steps of mixing a sample and a plurality of functionalized magnetic beads to form a sample fluid that causes the analyte to bind to the functionalized magnetic beads. The next step of the method is introducing the sample fluid with magnetic beads into an inclined capillary tube 122. The method continues by capturing the magnetic beads and analyte bound to them with the magnet 140 in the defined volume well 144 adjacent the inclined capillary tube 122 and adding a wash to the inclined capillary tube 122. Then as above an antibody to the target that is linked to an enzyme is introduced to bond to the analyte on the magnetic beads. The method then includes the steps of optionally adding another label to stick to the magnetic beads with bound analyte trapped at the magnet 140 in response to a target analyte being present for signal enhancement. Next, a developer solution is added to the inclined capillary tube 122. The method then includes the steps of reacting the labelled sample fluid magnetic beads having the bound enzyme and the developer solution and measuring the heat generated by the reaction between the magnetic beads with the bound target and enzyme and the developer using the calorimeter 142. The method concludes by confirming presence of the target analyte in the sample fluid in response to the measuring of heat by the calorimeter 142. The principles of the reaction in the developer are as described above.

Figure 3:
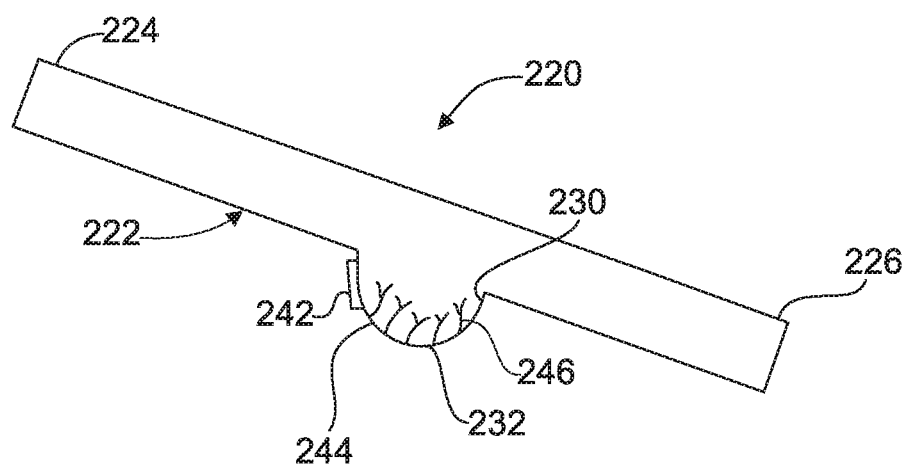
FIG. 3 illustrates a third embodiment of a device for detecting a target analyte according to aspects of the present disclosure.

A third embodiment 220 of a device for detecting a target analyte is shown in FIG. 3 and includes an inclined capillary tube 222 extending from a first end 224 to a second end 226. In more detail, the first end 224 is elevated above the second end 26 for transporting a sample fluid containing a sample.

A defined volume well 244 that has an open end 230 and a closed end 232 is coupled with the inclined capillary tube 222. The defined volume well 244 is disposed between the first end 224 and the second end 226 for receiving the sample fluid. A plurality of directly attached capture antibodies 246 directed to the target analyte are disposed in the defined volume well 244. The capture antibodies 246 are used to anchor the target analyte to the well. The process then proceeds using typical ELISA procedures to bind a second antibody to the target, this antibody having linked to it an enzyme. Alternatively one can use a third antibody, which is enzyme-linked, that recognizes the second antibody bound to the target analyte in a sandwich type ELISA assay process to detect the target analyte. Additionally, a calorimeter 242 is disposed adjacent the defined volume well 244 for receiving heat output from a reaction of the enzyme linked to the target analyte in the sample fluid through the above described attachment possibilities. In this system the capture antibodies 246 are taking the place of the magnetic beads in the first two embodiments. In this embodiment, functionalized magnetic beads are not used or necessary since the capture antibodies 246 can directly capture the target analyte from a sample.

A method of operating the third embodiment 220 of the device is also provided. The method includes the step of introducing a sample fluid into an inclined capillary tube 222. The method continues with the step of adding a wash to the inclined capillary tube 222. Then, adding a label, which has attached to it an enzyme, to the sample fluid to label a target analyte in response to the target analyte being present and attached to the capture antibodies 246. The next step of the method is adding a developer solution to the inclined capillary tube 222. Then, the method proceeds by the steps of reacting the labelled target analyte linked to the enzyme in the sample fluid and the developer solution and measuring heat generated by the reaction caused by the enzyme and the developer using a calorimeter 242. The method concludes with the step of confirming presence of the target analyte in the sample fluid in response to the measuring of heat from the reaction by the calorimeter 242.

Figure 4A:
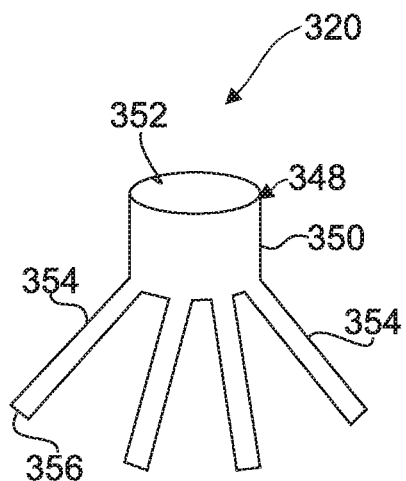
FIG. 4A and FIG. 4B illustrate a fourth embodiment of a device for detecting a target analyte according to aspects of the present disclosure, FIG. 4A provides a side view of a flow splitter according to the present disclosure
Figure 4B:
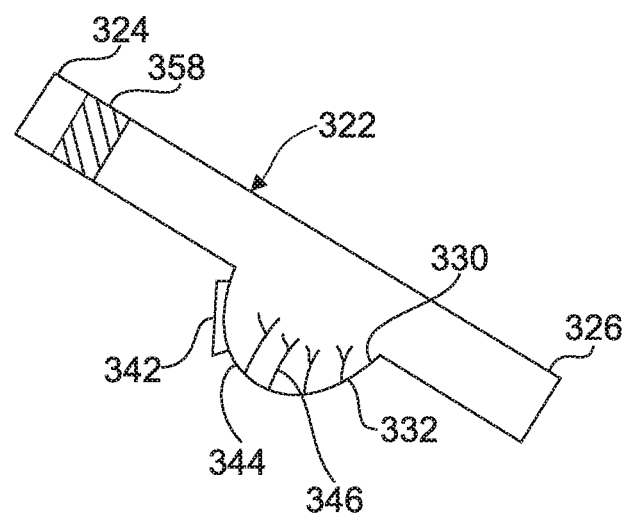

A fourth embodiment 320 of a device for detecting a target analyte is shown in FIG. 4A and FIG. 4B and includes a flow splitter 348 that has a main body 350 defining an inlet 352 and a plurality of channels 354 coupled to the main body 350. The plurality of channels 354 each define an outlet 356 for separating a sample fluid of a first volume containing a sample into a plurality of secondary fluid samples each having a volume less the first volume. This system allows for both the processing of the same sample for the presence of multiple targets and the ability to process a large volume of sample fluid as described below.

The channels 354 each include an inclined capillary tube 322 extending from a first end 324 to a second end 326. More specifically, the first end 324 is elevated above the second end 326 and is coupled to the outlet 356 of the channel 354 for transporting the secondary fluid sample containing a sample. The capillary tubes 322 each include a porous matrix 358 impregnated with a label for a target analyte and disposed in the inclined capillary tube 322 at the first end 324 for labelling target analyte in the secondary fluid sample. Optionally, the label for the target analyte can be conjugated to a magnetic bead and a magnet can be used to capture and move the anlyte through the system. Such direct labelling is most advantageous when multiplexing as done in the fourth embodiment, as compared to other embodiments. Each label can be to different targets or to the same target in each capillary tube 322 depending on whether the intent is to process a sample for the presence of multiple targets or to process a large volume of sample for the same analyte, respectively. The labels can have attached to them enzymes as described above. The channels 354 also each include a defined volume well 344 having an open end 330 and a closed end 332 and coupled with the inclined capillary tube 322. Each defined volume well 344 is disposed between the first end 324 and the second end 236 for receiving the secondary fluid sample. The use of the defined volume well 344 allows the device to trap a specific amount of the developer solution; this then provides thermal insulation needed for the reaction. The device can be constructed of plastic material which also helps to insulate the material and an air gap found above the defined volume well 344 is believed to provide results that are as sought after as using a "bead" of the fluid sample. This design is more straight-forward as it is not necessary to move magnetic beads around and into droplets. The defined volume wells 344 just must be consistent in volume within the device 320.

The channels 354 each include at least one of a plurality of directly attached capture antibodies 346 disposed in the defined volume well 344 or a magnet (not shown) is associated with the well 344, the capture antibodies 346 capture the target analyte by binding to it or to the label from the porous matrix 358 the magnet can be used to capture labels that are conjugated to magnetic beads as described above. Additionally, the channels 354 each include a calorimeter 342 disposed adjacent the defined volume well 344 for receiving heat output from a reaction between the enzyme linked to the target through one of the herein described methods and the developer solution.

A method of operating the third embodiment of the device is also provided. The method includes the step of introducing a sample fluid into a flow splitter 348. Next separating the sample fluid of a first volume containing a sample into a plurality of secondary fluid samples each having a volume less the first volume. The method proceeds by transporting each second fluid sample into one of a plurality of inclined capillary tubes 322. Then, the method includes the step of dissolving a label from a porous matrix 358 with the secondary fluid sample in each of the plurality of inclined capillary tubes 322 to label a target analyte in response to the target analyte being present. The labeled target analyte is trapped by the capture antibodies 346 and/or the magnet. The next step of the method is adding a developer solution to each of the plurality of inclined capillary tubes 322. The method proceeds by reacting each of the plurality of labelled secondary fluid samples and the developer solution and measuring heat generated by each of the reactions between the linked enzymes and the developer using a calorimeter 342. The method concludes with the step of confirming presence of the target analyte in each of the plurality of secondary fluid samples in response to the measuring of heat by each of the calorimeters 342 from the reactions.

As shown in FIG. 5A-5C a typical ELISA reaction scheme is utilized in the present disclosure. In the scheme an enzyme is linked to an antibody and the antibody is use in either a typical direct ELISA process or a sandwich ELISA process. Once the antibody with the enzyme linked to it is bound adding a reaction solution containing substrate for the enzyme allows the enzyme to carry out its enzymatic process and the heat of reaction produced by this reaction is measured by the nanocalorimeter in the present disclosure. In this scheme the target analyte is the antigen as shown in the figures.

Clearly, changes may be made to what is described and illustrated herein without, however, departing from the scope defined in the accompanying claims. The device and method for detecting a target analyte may be employed for other types of applications besides those described herein, for example.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure. Those skilled in the art will recognize that concepts disclosed in association with an example switching system can likewise be implemented into many other systems to control one or more operations and/or functions.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated degrees or at other orientations) and the spatially relative descriptions used herein interpreted accordingly.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for detection of a target analyte by an Enzyme-Linked Immunosorbent Assay (ELISA) comprising:
    a capillary tube that includes a first end and a second end and a well located between said first end and said second end of said capillary tube and said capillary tube moving fluids from said first end to said well and said second end;
    said well further includes a frangible protective film over an opening of said well, said protective film sealing said opening of said well and wherein said opening connects said well to said capillary tube;
    a calorimeter attached to said well, said calorimeter adapted to detect a change in a temperature in said well; and a magnet.

2. The system as recited in claim 1 wherein said magnet is movable along an outside of said capillary tube and said well and wherein said magnet can move magnetic beads from said first end to inside said well.

3. The system as recited in claim 1 wherein said magnet is secured to a bottom of said well, said magnet capable of attracting magnetic beads from said capillary tube into said well.

4. The system as recited in claim 1 further comprising a button and a puncture needle, said button and puncture needle capable of breaking said frangible film to allow communication between an inside of said capillary tube and said well.

5. The system as recited in claim 1 further comprising a plurality of magnetic beads, said beads capable of binding a target analyte through a label conjugated to said magnetic beads and being capable of binding said target analyte.

6. The system as recited in claim 1 wherein said magnet is an electromagnet.

7. The system as recited in claim 1 wherein said system is washable and reusable.

\* \* \* \* \*